US009629733B2

(12) United States Patent
Roeder et al.

(10) Patent No.: US 9,629,733 B2
(45) Date of Patent: Apr. 25, 2017

(54) STENTS HAVING BARBS PROTECTED DURING DELIVERY

(71) Applicant: Cook Medical Technologies LLC, Bloomington, IN (US)

(72) Inventors: Blayne A. Roeder, Bloomington, IN (US); Siddharth Vad, Bloomington, IN (US)

(73) Assignee: Cook Medical Technologies LLC, Bloomington, IN (US)

( * ) Notice: Subject to any disclaimer, the term of this patent is extended or adjusted under 35 U.S.C. 154(b) by 0 days.

(21) Appl. No.: 14/969,281

(22) Filed: Dec. 15, 2015

(65) Prior Publication Data

US 2016/0095725 A1  Apr. 7, 2016

Related U.S. Application Data

(62) Division of application No. 13/836,772, filed on Mar. 15, 2013, now Pat. No. 9,254,204.

(51) Int. Cl.
*A61F 2/06* (2013.01)
*A61F 2/848* (2013.01)
(Continued)

(52) U.S. Cl.
CPC ............ *A61F 2/848* (2013.01); *A61F 2/844* (2013.01); *A61F 2/915* (2013.01); *A61F 2/91* (2013.01); *A61F 2002/075* (2013.01); *A61F 2002/8483* (2013.01); *A61F 2002/8486* (2013.01); *A61F 2002/9505* (2013.01);
(Continued)

(58) Field of Classification Search
CPC .... A61F 2/915; A61F 2/89; A61F 2/82; A61F 2/07; A61F 2/848; A61F 2002/91558; A61F 2002/8483; A61F 2002/075
See application file for complete search history.

(56) References Cited

U.S. PATENT DOCUMENTS

2009/0264992 A1* 10/2009 Fleming, III ............. A61F 2/07
623/1.36

FOREIGN PATENT DOCUMENTS

EP  2 111 828 A2  10/2009
EP  2 517 672 A1  10/2012
(Continued)

OTHER PUBLICATIONS

Partial European Search Report dated Feb. 3, 2015 for Patent Application No. EP 14275055, pp. 1-8.
(Continued)

*Primary Examiner* — Thomas J Sweet
*Assistant Examiner* — Tiffany Shipmon
(74) *Attorney, Agent, or Firm* — Brinks Gilson & Lione

(57) ABSTRACT

The present embodiments provide a method for delivering a stent comprising providing a stent in a delivery state, where the stent comprises a plurality of interconnected strut segments that enable expansion of the stent from a delivery state to a deployed state. Stacking a frontal surface of a first strut segment at least partially behind a rear surface of a second strut segment in the delivery state. Aligning a sharpened tip of a first barb at least partially circumferentially behind at least one strut segment in the delivery state such that the sharpened tip is not radially exposed. Expanding the stent from the delivery state to a deployed state, wherein the first barb is exposed to a patient in the deployed state.

19 Claims, 7 Drawing Sheets

(51) Int. Cl.
*A61F 2/844* (2013.01)
*A61F 2/915* (2013.01)
A61F 2/95 (2013.01)
A61F 2/91 (2013.01)
A61F 2/07 (2013.01)

(52) U.S. Cl.
CPC ............. *A61F 2220/0016* (2013.01); *A61F 2250/0037* (2013.01); *A61F 2250/0063* (2013.01); *A61F 2250/0098* (2013.01)

(56) References Cited

FOREIGN PATENT DOCUMENTS

| WO | WO 01/06952 A1 | 2/2001 |
| WO | WO 2007/100716 A2 | 9/2007 |
| WO | WO 2009/042789 A2 | 4/2009 |
| WO | WO 2009/149457 A1 | 12/2009 |

OTHER PUBLICATIONS

European Examination Report dated Feb. 2, 2017, for European Application No. 14 275 055.3-1664, 5 pages.

\* cited by examiner

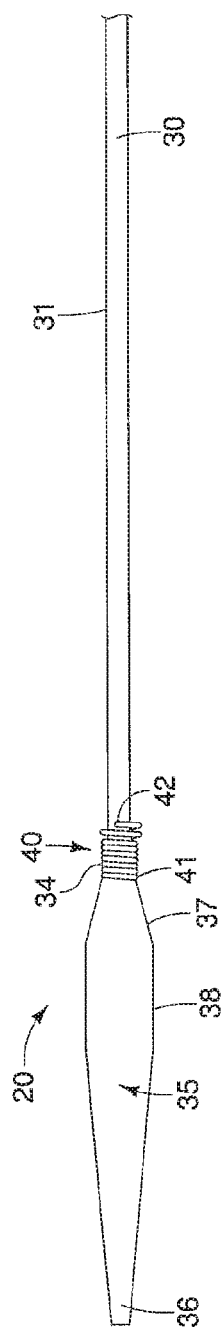
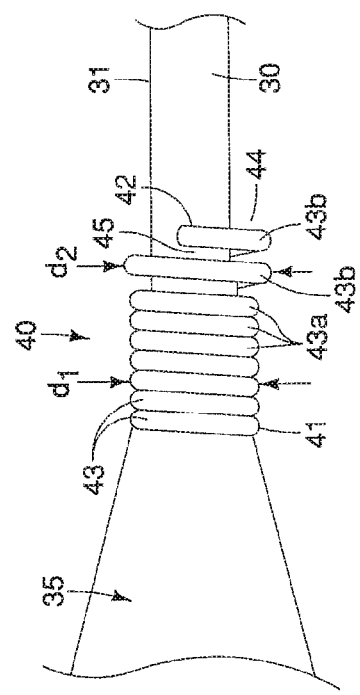
FIG. 1
FIG. 2

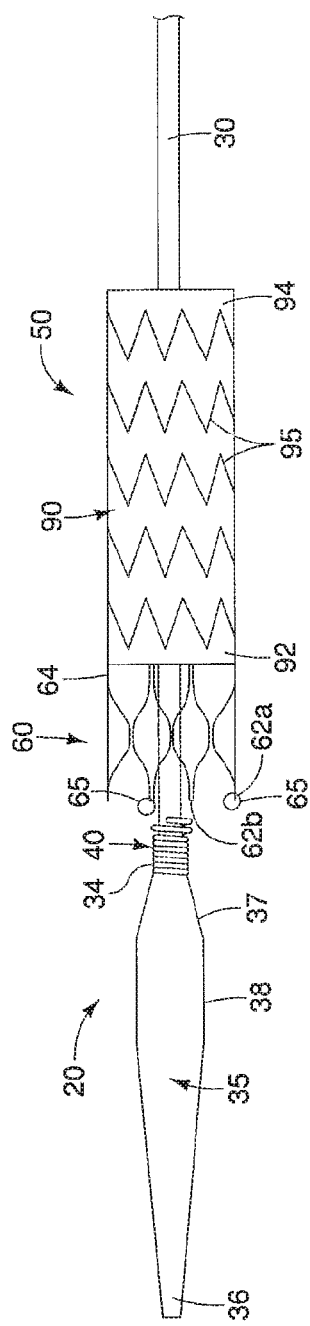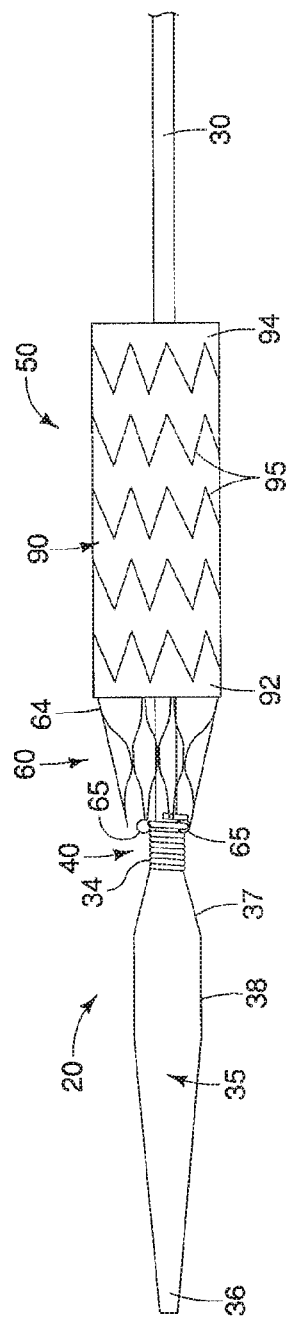

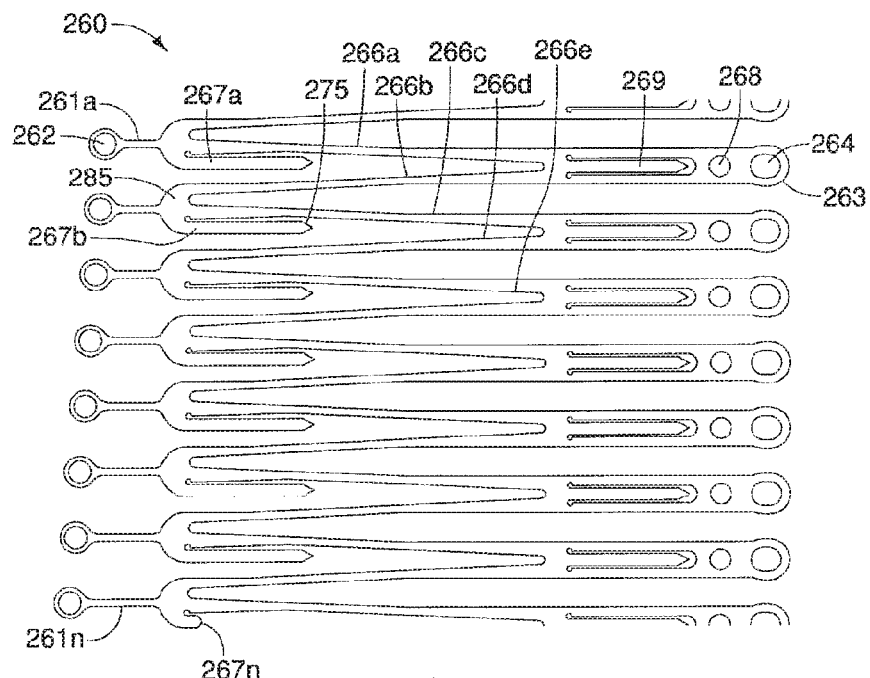
FIG. 11
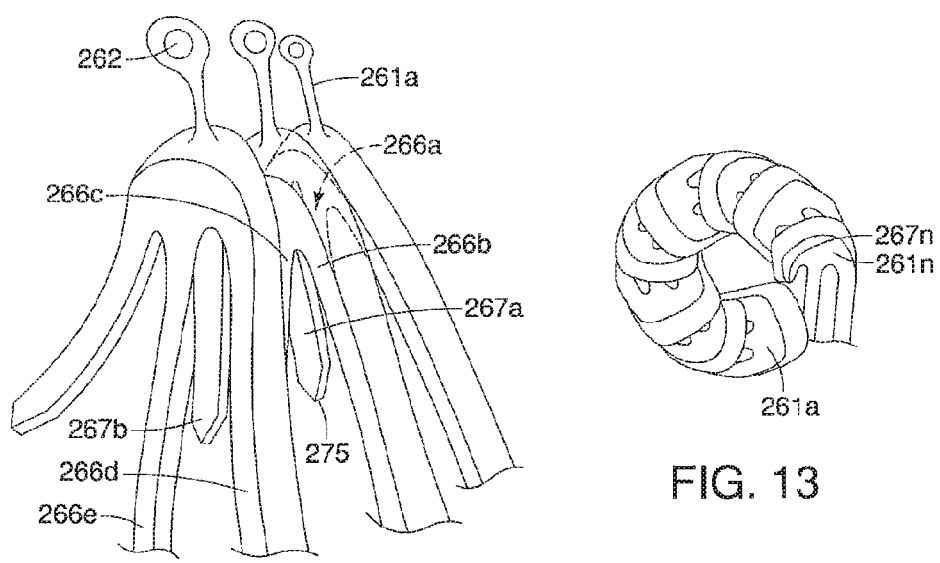
FIG. 12
FIG. 13

STENTS HAVING BARBS PROTECTED DURING DELIVERY

CROSS-REFERENCE TO RELATED APPLICATIONS

This application is a divisional of U.S. application Ser. No. 13/836,772, filed on Mar. 15, 2013, the entirety of which is hereby incorporated by reference.

BACKGROUND

The present embodiments relate generally to medical devices, and more specifically, to stents having barbs protected during delivery.

Stents may be inserted into an anatomical vessel or duct for various purposes. Stents may maintain or restore patency in a formerly blocked or constricted passageway, for example, following a balloon angioplasty procedure. Other stents may be used for different procedures, for example, stents placed in or about a graft have been used to hold the graft in an open configuration to treat an aneurysm. Additionally, stents coupled to one or both ends of a graft may extend proximally or distally away from the graft to engage a healthy portion of a vessel wall away from a diseased portion of an aneurysm to provide endovascular graft fixation.

Stents may be either self-expanding or balloon-expandable, or they can have characteristics of both types of stents. Self-expanding stents may be delivered to a target site in a compressed configuration and subsequently expanded by removing a delivery sheath, removing trigger wires and/or releasing diameter reducing ties. With self-expanding stents, the stents expand primarily based on their own expansive force without the need for further mechanical expansion. In a stent made of a shape-memory alloy such as nitinol, the shape-memory alloy may be employed to cause the stent to return to a predetermined configuration upon removal of the sheath or other device maintaining the stent in its predeployment configuration.

Typically, the actuation of the trigger wire or other mechanism restraining a stent causes an immediate, full radial expansion of the stent, such that the stent engages an inner wall of a duct, vessel or the like. Barbs of the stent may engage the body passage, and the deployed stent may be difficult or impossible to recapture or reposition at this time.

SUMMARY

The present embodiments provide a stent comprising a plurality of interconnected strut segments that enable expansion of the stent from a delivery state to a deployed state. A first strut segment and a second strut segment, of the plurality of strut segments, each comprise frontal surfaces facing radially inward in the deployed state and rear surfaces facing radially outward in the deployed state. The frontal surface of the first strut segment is at least partially stacked behind the rear surface of the second strut segment in the delivery state. A first barb coupled to at least a portion of the first strut segment. A sharpened tip of the first barb is aligned at least partially circumferentially behind at least one strut segment in the delivery state such that the sharpened tip is not radially exposed.

In one embodiment, the first barb is disposed at least partially laterally between the first and second strut segments in the deployed state. The first barb further is at least partially disposed on an opposing side of the second strut segment in the delivery state. In one example, a majority of the first barb may be disposed on the opposing side of the second strut segment and longitudinally adjacent to the second strut segment in the delivery state.

The stent further may comprise a third strut segment, wherein portions of the second and third strut segments meet up with one another to form a proximal apex of the stent. The third strut segment is on a side of the second strut segment opposing the first strut segment. At least a portion of the first barb is disposed between the second and third strut segments in the delivery state. A fourth strut segment, disposed on a side of the third strut segment opposing the second strut segment, may at least partially circumferentially cover the first barb in the delivery state. A final strut segment to be loaded to a delivery system comprises one of a rounded or blunt or missing barb.

In one embodiment, the stent may be configured to be releasably secured to a portion of a coiled member during delivery. One of proximal or distal ends of the stent comprises a plurality of apices that each comprises a coupling member that is releasably secured to the coiled member. Longitudinal positions of the coupling members of adjacent apices may be axially staggered relative to each other. The axial staggering length differential between adjacent apices may be calculated based on a formula factoring into account at least the pitch of the coiled member.

Other systems, methods, features and advantages of the invention will be, or will become, apparent to one with skill in the art upon examination of the following figures and detailed description. It is intended that all such additional systems, methods, features and advantages be within the scope of the invention, and be encompassed by the following claims.

BRIEF DESCRIPTION OF THE DRAWINGS

The invention can be better understood with reference to the following drawings and description. The components in the figures are not necessarily to scale, emphasis instead being placed upon illustrating the principles of the invention. Moreover, in the figures, like referenced numerals designate corresponding parts throughout the different views.

FIG. 1 is a side view of a first embodiment of an apparatus for deploying a portion of a stent using at least one coiled member.

FIG. 2 is an enlarged view of the coiled member of FIG. 1.

FIGS. 4-5 are side views depicting coupling of the stent-graft of FIG. 3 to the apparatus of FIGS. 1-2.

FIG. 11 is a side view of a further alternative stent, shown in a flattened and compressed state, which has barbs that are protected during delivery.

FIG. 12 is a perspective view schematically showing a portion of the stent of FIG. 11 and depicting protection of multiple barbs during delivery.

FIG. 13 is a top view of a portion of the stent of FIGS. 11-12 in a delivery state.

DETAILED DESCRIPTION OF THE PREFERRED EMBODIMENTS

Figure 3:
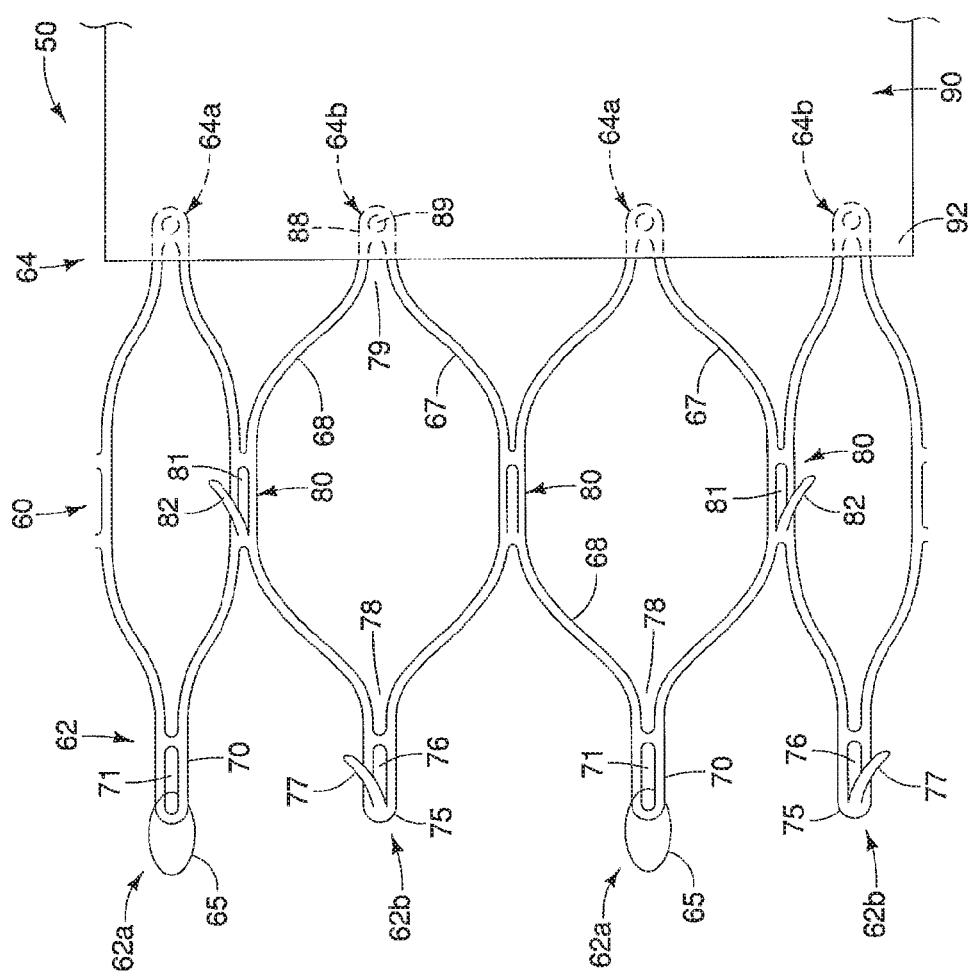
FIG. 3 depicts an exemplary stent-graft having a portion that may be deployed using the coiled member of FIGS. 1-2.

In the present application, the term "proximal" refers to a direction that is generally closest to the heart during a medical procedure, while the term "distal" refers to a direction that is furthest from the heart during a medical procedure.

Referring to FIGS. 1-2, a first embodiment of an apparatus 20 is shown for deploying a portion of a stent using at least one coiled member. The apparatus 20 generally comprises a cannula 30 having an outer surface 31, and at least one coiled member 40 having a region that is secured to the outer surface 31 of the cannula 30.

The cannula 30 may be incorporated as part of a broader stent or stent-graft delivery system, and may span a longitudinal length in which a distal segment extends outside of a patient's body, and a proximal segment 34, including the coiled member 40, is delivered towards a target site inside of a patient's body. The cannula 30 may be used as an inner cannula, to the extent that one or more outer cannulas or sheaths are disposed coaxially over the cannula 30. For example, a stent-graft may be disposed over an exterior surface of the cannula 30 and within one or more outer cannulas or sheaths, thereby encompassing the stent-graft during a delivery stage.

The cannula 30 may comprise a tubular member having a lumen sized to allow the cannula 30 to be advanced over a wire guide during delivery. A proximal region of the cannula 30 may be integrally formed with, or externally coupled to, an atraumatic tip 35. The atraumatic tip 35 may comprise proximal and distal regions 36 and 37, respectively, and a central region 38 disposed therebetween. The proximal and distal regions 36 and 37 comprise a smaller outer diameter relative to the central region 38, with a first taper allowing for a smooth transition between the proximal region 36 and the central region 38, and a second taper allowing for a smooth transition between the distal region 37 and the central region 38.

The coiled member 40 comprises a proximal end 41, a distal end 42, and a plurality of turns 43 disposed therebetween, as shown in FIGS. 1-2. In this non-limiting example, the proximal end 41 of the coiled member 40 is secured to the outer surface 31 of the cannula 30 using a suitable mechanism, such as a solder, weld, mechanical attachment, friction fit, crimp, or combination of these or other techniques and mechanisms. Accordingly, the proximal end 41 of the coiled member 40 cannot move relative to the outer surface 31 of the cannula 30. The proximal end 41 of the coiled member 40 comprises a first diameter $d_1$, which may be approximately the same diameter, or slightly greater than, an outer diameter of the cannula 30.

The distal end 42 of the coiled member 40 is unsecured relative to the outer surface 31 of the cannula 30, as shown in FIGS. 1-2. The distal end 42 of the coiled member 40 may comprise a second diameter $d_2$, which is greater than the first diameter $d_1$ of the proximal end 41 of the coiled member 40. There is a separation or gap 44 between the distal end 42 of the coiled member 40 and the outer surface 31 of the cannula 30, as best seen in FIG. 2.

The plurality of turns 43 are divided into a proximal series of turns 43a, which have the first diameter $d_1$, and a distal series of turns 43b, which have the second diameter $d_2$. The proximal series of turns 43a may be disposed in close proximity or abutting one another, as depicted in FIG. 2. By contrast, the distal series of turns 43b may be spaced apart from one another a greater distance than the proximal series of turns 43a. In FIG. 2, the distal series of turns 43b are spaced apart a predetermined distance denoted by spacing 45. As will be described further in FIGS. 4-5 below, a portion of a stent 60 may be coupled to at least one of the distal series of turns 43b, and secured within the spacing 45 between adjacent distal turns.

The exemplary coiled member 40 may be formed from stainless steel, nitinol, titanium, or other suitable biocompatible materials. If manufactured from nitinol, the unsecured end of the coiled member may be heat-set so that it contracts around the outer surface 31 of the cannula 30 when disposed within the body, thereby reducing the likelihood of the coiled member 40 snagging the stent 60 or other components. In one example, the coiled member 40 is formed from a material that has radiopaque properties.

Referring now to FIG. 3, an exemplary stent-graft 50, having a proximally-located stent 60 coupled to a graft material 90, may be deployed in a controlled manner using the coiled member 40 of FIGS. 1-2, as shown further in the exemplary coupling sequence of FIGS. 4-5 below. In this non-limiting embodiment, the stent 60 may be manufactured from a continuous cylinder into which a pattern may be cut by a laser or by chemical etching to produce slits in the wall of the cylinder. The resulting structure may then be heat set to give it a desired final configuration. As shown in FIG. 3, the final configuration may include a shape having a series of proximal apices and a series of distal apices. A proximal end 62 of the stent 60 may comprise multiple adjacent proximal apices 62a and 62b, while a distal end 64 of the stent 60 may comprise multiple adjacent distal apices 64a and 64b, as shown in FIG. 3.

In FIG. 3, at least one pair of adjacent, proximal apices 62a and 62b may comprise different features. For example, as shown in FIG. 3, a first proximal apex 62a may comprise an end region 70 having a bore 71 formed therein, wherein the bore 71 is configured to receive a suture loop 65, as explained further below. A second, adjacent proximal apex 62b may comprise an end region 75 having an integral barb 77 formed therein, as shown in FIG. 3. The barb 77 may be formed by laser cutting a desired barb shape into the end regions 75. A slit 76 therefore is formed into each end region 75 after the desired barb shape is formed, as shown in FIG. 3. Once the desired barb shape is cut, a main body of the barb 77 may be bent in a radially outward direction with respect to the end region 75. The angle may comprise any acute angle, or alternatively may be substantially orthogonal or obtuse. If desired, the barb 77 may be sharpened, for example, by grinding the tip of the barb, to facilitate engagement at a target tissue site.

Referring still to FIG. 3, the stent 60 may comprise at least one strut segment disposed between the proximal and distal apices. For example, multiple angled strut segments may be disposed between a first proximal apex 62a and a corresponding distal apex 64a, and an identical set of angled strut segments may be disposed between an adjacent, second proximal apex 62b and a corresponding distal apex 64b. By way of example, a first proximal apex 62*a* extends distally and splits into first and second angled strut segments 67 and 68, respectively, thereby forming a proximal vertex 78, as shown in FIG. 3. In a compressed state, the first and second angled strut segments 67 and 68 may be compressed such that they are substantially parallel to one another. Similarly, each distal apex 64*a* and 64*b* may extend in a proximal direction and split into the first and second angled strut segments 67 and 68, respectively, thereby forming a distal vertex 79. A first angled strut segments 67 may meet with an adjacent second angled strut segment 68, thereby forming a transition region 80. In this manner, the stent 60 may be formed into a continuous, generally cylindrical shape, as shown in FIG. 3.

Expansion of the stent 60 is at least partly provided by the angled strut segments 67 and 68, which may be substantially parallel to one another in a compressed state, but may tend to bow outward away from one another in the expanded state shown in FIG. 3. The stent 60 may be formed from any suitable material, such as a laser-cut nitinol cannula. If manufactured from nitinol, the stent 60 may be inclined to assume the expanded state shown in FIG. 3 upon removal of a delivery sheath or engagement with the coiled member 40, as explained in FIGS. 4-5 below.

Each transition region 80 may comprise a larger surface area relative to the angled segments, since the transition regions are composed substantially of multiple different angled segments 67 and 68. The stent 60 may comprise at least one barb 82 disposed in at least one of the transition regions 80. The barb 82 may be formed integrally, as part of the strut, or may comprise an external barb that is adhered to a surface of the transition regions 80. As shown in FIG. 3, multiple integral barbs 82 are provided. Like the barbs 77 noted above, the barbs 82 may be formed by laser cutting a desired barb shape into the transition regions 80. A slit 81 therefore is formed into the transition region 80 after the desired barb shape is formed, as shown in FIG. 3. Since the transition regions 80 may comprise an increased surface area relative to other regions of the stent 60, it may be easier to perforate portions of the transition regions 80 without adversely affecting the structural integrity of the stent. Once the desired barb shape is cut, a main body of the barb 82 may be bent in an outward direction at any angle with respect to the transition region 80 and optionally may be sharpened to facilitate engagement at a target tissue site.

Each of the distal apices 64*a* and 64*b* may comprise an end region 88 having a bore 89 formed therein, as shown in FIG. 3. The distal end 64 of the stent 60 may be coupled to a proximal end 92 of the graft material 90. The distal apices 64*a* and 64*b* may be coupled to the graft material, for example, using one or more sutures that are looped through the graft material and the bores 89 of the stent 80. In this manner, the stent 60 may be used as an attachment stent for endovascular graft fixation. For example, the graft material 90 may overlap with an aneurysm to seal off fluid flow into the aneurysm, while the proximal end 62 of the stent 60 may extend in a proximal direction away from the graft material, e.g., to engage a healthy portion of a vessel wall away from a diseased portion of the aneurysm. As will be apparent, one or more additional stents may be coupled to an inner or outer surface of the graft material 90, i.e., at a location distal to the stent 60, to help maintain patency throughout the graft material. While multiple exemplary zig-zag stents 95 are shown coupled to the graft material 90 between the proximal and distal ends 92 and 94 of the graft material 90 in FIGS. 4-5, it will be apparent than any shape of stent may be used, and such stents may be coupled to either the inner or outer surfaces of the graft material 90.

The stent 60 has a reduced diameter delivery state so that it may be advanced to a target location within a vessel or duct. The stent 60 also has an expanded deployed state to apply a radially outward force upon at least a portion of a vessel or duct, e.g., to maintain patency within a passageway, or to hold open the lumen of a graft. In the expanded state, fluid flow is allowed through a central lumen of the stent 60. Further, the struts of the stent 60 may comprise a substantially flat wire profile or may comprise a rounded profile. As best seen in FIG. 3, the struts of the stent 60 generally comprise a flat wire profile.

The stent 60 may be manufactured from a super-elastic material. Solely by way of example, the super-elastic material may comprise a shape-memory alloy, such as a nickel titanium alloy (nitinol). If the stent 60 comprises a self-expanding material such as nitinol, the stent may be heat-set into the desired expanded state, whereby the stent 60 can assume a relaxed configuration in which it assumes the preconfigured first expanded inner diameter upon application of a certain cold or hot medium. Alternatively, the stent 60 may be made from other metals and alloys that allow the stent 60 to return to its original, expanded configuration upon deployment, without inducing a permanent strain on the material due to compression. Solely by way of example, the stent 60 may comprise other materials such as stainless steel, cobalt-chrome alloys, amorphous metals, tantalum, platinum, gold and titanium. The stent 60 also may be made from non-metallic materials, such as thermoplastics and other polymers.

While one exemplary stent 60 is shown in FIG. 3 and described in FIGS. 4-5 below, various alternative stent configurations may be used in conjunction with the coiled member 40 of FIGS. 1-2. Moreover, the stent may be deployed alone, or as part of a stent-graft system, as depicted herein.

Referring now to FIGS. 4-5, an exemplary coupling of the stent-graft 50 of FIG. 3 to the deployment apparatus of FIGS. 1-2 is shown and described. The stent-graft 50 has an uncoupled state in which the stent-graft 50 is positioned coaxially over the cannula 30 with the proximal end 62 of the stent 60 in longitudinal proximity relative to the distal end 42 of the coiled member 40, as shown in FIG. 4. During assembly, the suture loops 65 that are coupled to the proximal apices 62*a* of the stent 60 are threaded around the distal end 42 of the coiled member 40 one at a time, preferably until all of the suture loops 65 are coupled to the coiled member 40. Such coupling may be achieved by rotating the cannula 30 in a clockwise direction until the proximal end 62 of the stent 60 is sufficiently compressed in a radially inward direction, as depicted in FIG. 5. It should be noted that the gap 44 between the distal end 42 of the coiled member 40 and the outer surface 31 of the cannula 30 permits positioning of the suture loops 65 around the distal series of turns 43*b*.

The suture loops 65 are further accommodated within the spacing 45 between the distal series of turns 43*b*. The suture loops 65 preferably are coupled to the coiled member 40 in a manner in which at least one suture loop 65 is positioned around at least one full turn of the distal series of turns 43*b*, and preferably around at least 1.5 turns at the distal end 42 of the coiled member 40, thereby reducing the likelihood of inadvertent uncoupling of the suture loops 65 from the coiled member 40.

The coupling shown in FIG. 5 secures the stent 60 to the cannula 30 via the coiled member 40 in a manner that may subsequently facilitate insertion of the subassembly comprising the cannula 30 and the stent-graft 50 into an outer sheath. As will be apparent, the outer sheath is configured to radially restrain other regions of the stent-graft 50 for delivery to a target site within a patient's anatomy.

In this embodiment, the suture loops 65 are coupled to every other proximal apex 62a to restrain the stent 60 during delivery. The suture loops 65 are not coupled to the second proximal apices 62b, which comprise the barbs 77. By restraining the alternating proximal apices 62a using the suture loops 65 coupled to the coiled member 40, the adjacent second proximal apices 62b also may be indirectly pulled in a radially inward direction during delivery. The configuration of the stent 60, and in particular the angled segments 67 and 68 that meet up at transition regions 80, facilitates the indirect compression of the adjacent second proximal apices 62b. Since only selected ones of the proximal apices are restrained during delivery, the number of suture loops 65 may be reduced. Moreover, since the barbs 77 are only disposed on every other apex, barb entanglement may be reduced or eliminated.

An introducer, similar to that described in PCT application WO98/53761, entitled "A Prosthesis and a Method and Means of Deploying a Prosthesis," which is incorporated herein by reference in its entirety, may be used to deploy the stent-graft 50. PCT application WO98/53761 describes a deployment system for an endoluminal prosthesis whereby the prosthesis is radially compressed onto a delivery catheter and is covered by an outer sheath. To deploy the system, the operator slides or retracts the outer sheath over the delivery catheter, thereby exposing the prosthesis. The prosthesis expands outwardly upon removal of the sheath. The operator can directly manipulate the sheath and the delivery catheter, which provides the operator with a relatively high degree of control during the procedure. However, in the current embodiments, trigger wires and any of their associated sleeves would not be necessary to deploy the stent-graft 50. The stent-graft 50 may be positioned coaxially between the cannula 30 and the outer sheath. A mechanism, such as a pin vise, may be employed to prevent inadvertent rotation of the cannula 30 prior to the intended rotation as described in the present application.

In the present embodiments, a wire guide may be advanced to the target site, and the cannula 30 may be advanced over the wire guide to position the apparatus 20 at the desired location in proximity to the target site, with the atraumatic tip 35 reducing the likelihood of injury to bodily passageways during delivery. The outer sheath is disposed over the cannula 30 and the stent-graft 50 during insertion to the target site. Upon proper positioning at the target site using a desired imaging modality, the outer sheath is then retracted to expose at least a portion of the stent 60.

When the stent 60 is at least partially exposed, and it is desirable to deploy the proximal end 62 of the stent 60, the cannula 30 may be rotated in a counter-clockwise direction until the suture loops 65 are uncoupled from the coiled member 40, i.e., in a reverse manner from which the suture loops 65 were coupled to the coiled member 40. The stent 60 then may be deployed as shown in FIG. 4, and the remainder of the stent-graft 50 may be deployed by further retraction of the outer sheath or actuation of any other devices that are radially constraining the remainder of the stent-graft 50.

Advantageously, the proximal end 62 of the stent 60 is radially restrained without the use of convention trigger wires that span a full longitudinal length of the delivery system. Accordingly, the radial profile of the delivery system may be reduced without the provision of multiple trigger wires and one or more associated sleeves to house the trigger wires, thereby reducing packing density of the system. Moreover, deployment may be simplified as reduced deployment forces are expected to be needed relative to the use of conventional trigger wires.

As a further advantage, deployment of the stent 50 using the apparatus 20 comprising at least one coiled member 40 may allow for more precise positioning of the stent 50. In particular, deployment using the coiled member 40 may provide a more controlled unwinding of the associated portion of the stent 50, whereas the release of conventional trigger wires may require higher deployment forces that can cause a portion of the stent to jump longitudinally, thereby potentially deploying the stent offset from the intended target site.

Figure 7:
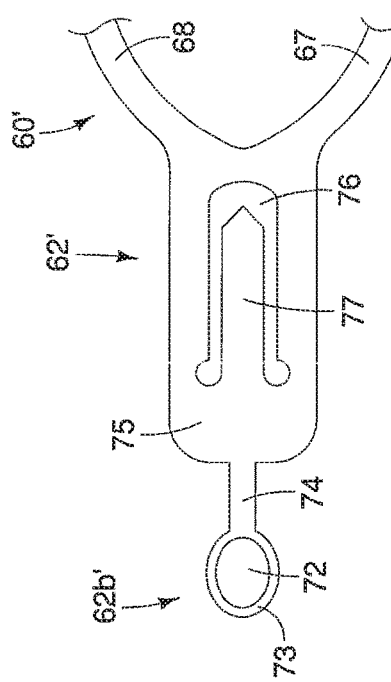
FIGS. 7-8 are side views depicting twisting of a portion of the proximal apex of the stent of FIG. 6.
Figure 8:
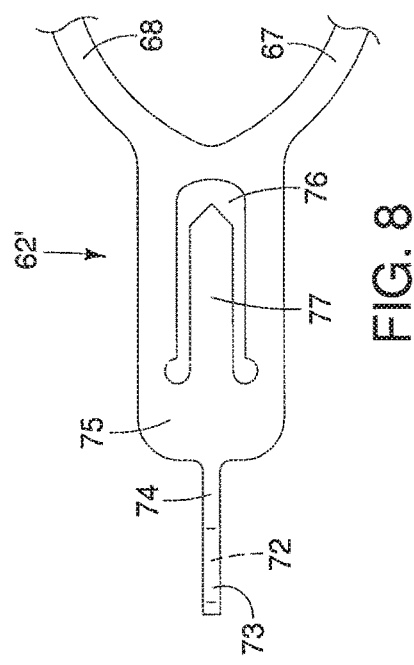
Figure 6:
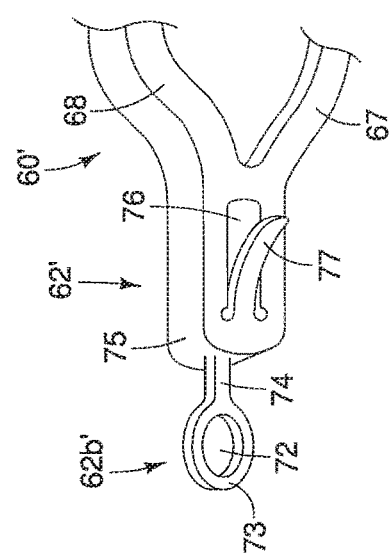
FIG. 6 is a perspective view of a proximal apex of a stent that may be coupled to a coiled member.

Referring now to FIGS. 6-8, a portion of an alternative stent 60' is described for use with the apparatus 20 comprising at least one coiled member 40 as described in FIGS. 1-2 and FIGS. 4-5. The alternative stent 60' is similar to the stent 60 of FIG. 3, with a main exception that an alternative proximal end 62' comprises at least one alternative proximal apex 62b' having an region comprising an eyelet 72.

The eyelet 72 may be formed within a ring portion 73 that is disposed at the proximal end of a proximal extension segment 74. The proximal extension segment 74 extends in a proximal direction away from the end region 75 having the integral barb 77, as shown in FIGS. 6-8.

In accordance with one aspect, the ring portion 73 and the proximal extension segment 74 comprise a wall thickness that is less than a wall thickness of the end region 75 having the integral barb 77, as best seen in FIG. 6. Advantageously, the reduced wall thickness of the ring portion 73 and the proximal extension segment 74 allows at least the ring portion 73 to twist in a circumferential direction to facilitate loading of the proximal apex 62' around the coiled member 40. In the example shown, the ring portion 73 twists in a circumferential direction about 90 degrees between a first state shown in FIG. 7 and a second state shown in FIG. 8. As will be apparent, the ring portion 73 may twist greater or less than 90 degrees, and the exemplary depiction between the states of FIGS. 7 and 8 is not intended to be limiting. Moreover, at least a portion of the proximal extension segment 74 may twist in the circumferential direction. The proximal extension segment 74 may twist a greater amount proximally since it is further from attachment from the end region 75 having the greater wall thickness.

As another advantage, the proximal extension segment 74 provides longitudinal separation of the ring portion 73 housing the eyelet 72 from the end region 75 having the integral barb 77. Accordingly, when the eyelet 72 is threaded around the coiled member 40, the proximal extension segment 74 provides a longitudinal spacing that reduces the likelihood of entanglement between the coiled member 40 and the integral barb 77 of the end region 75.

In the example of FIGS. 6-8, the ring portion 73 and the proximal extension segment 74 may be integrally formed with the end region 75. If the stent 60' is formed from nitinol or a similar material, the superelastic properties of such material can facilitate circumferential twisting of the ring portion 73 between the first and second states shown in FIGS. 7 and 8.

The alternative proximal apex 62b' shown in FIGS. 6-8 may be provided on each and every proximal apex of the stent 60'. Alternatively, the alternative proximal apex 62b' may be provided on fewer than all of the proximal apices of the stent 60', and the remaining proximal apices may be provided with only barbs, e.g., as depicted by the proximal apices 62b in FIG. 3 above, or the proximal apices may comprise other features.

Figure 10:
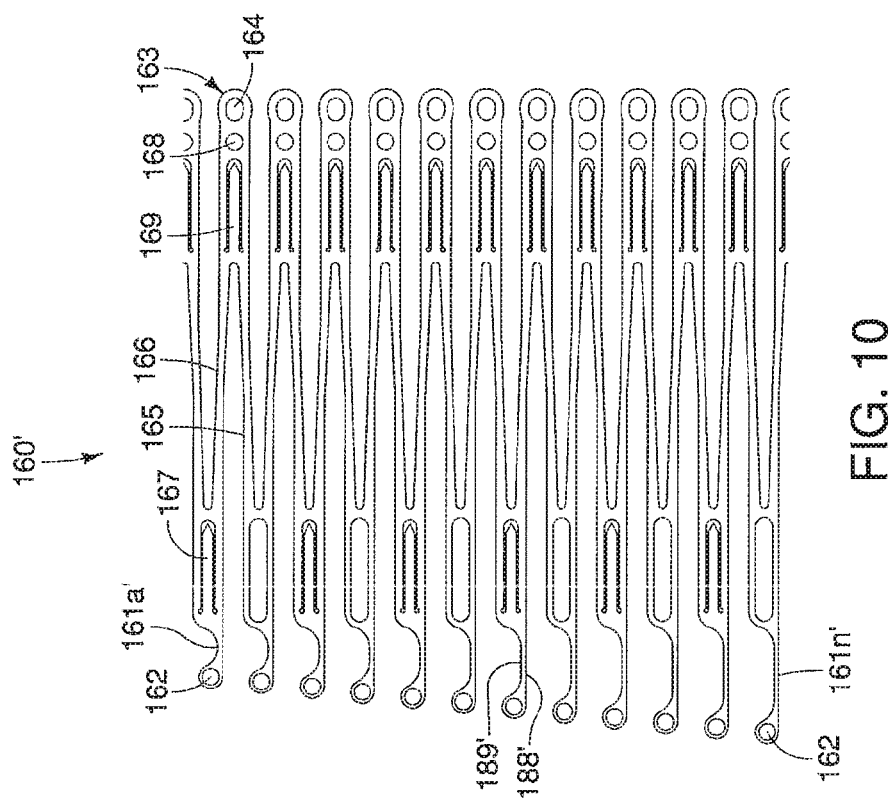
FIG. 10 is a side view of an alternative stent, shown in a flattened and compressed state, which is suitable for deployment using a coiled member.
Figure 9:
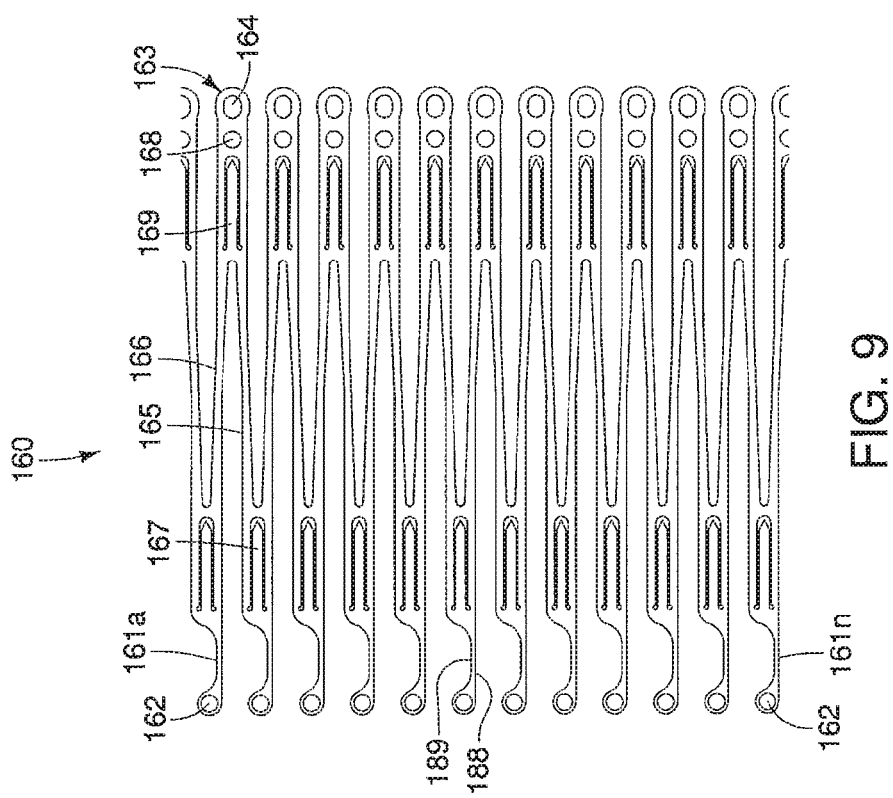
FIG. 9 is a side view of a stent, shown in a flattened and compressed state, which is suitable for deployment using a coiled member.

Referring now to FIGS. 9-10, two different stent designs are shown, which are alternatives to the stent 60 described above. In FIG. 9, a stent 160, which is shown in a flattened and compressed state, comprises a series of proximal apices 161 and a series of distal apices 163. Each of the proximal and distal apices 161 and 163 are separated by a plurality of strut segments 165 and 166, which enable radial expansion from the compressed state shown in FIG. 9 to a generally cylindrical expanded state similar to the stent 60 depicted in FIG. 4.

Each of the proximal apices 161 may comprise a coupling member 162, which is similar to the coupling member as explained in FIGS. 6-8 above having an eyelet 72, a ring portion 73 and an extension segment 74. Each of the proximal apices 161 further comprises an integral barb 167. Each of the distal apices 163 comprises a suture bore 164, an imaging marker 168, and an integral barb 169. The suture bore 164 overlaps with graft material 90, described and shown above, and allows suturing of a portion of each distal apex 163 to the graft material 90. The imaging marker 168, which is disposed proximal to the suture bore 164, may be aligned precisely with the proximal edge of the graft material 90 to enable precise placement of the proximal edge under an imaging modality.

The stent 160 may comprise any number 161n of proximal apices 161, where "n" is the number of apices. In the example of FIG. 9, "n" is equal to twelve, and each of the twelve proximal apices 161a through 161n have identical characteristics, including axial lengths. A first proximal apex 161a is loaded onto the coiled member 40 in the manner described above via engagement with the coupling member 162, and each subsequent proximal apex 161 is secured to the coiled member 40 until the final proximal apex 161n is secured to the coiled member. It should be noted that each of the proximal apices 161a through 161n comprises a region having a relatively thin strut segment 188, having a notched region 189 formed therein, which advantageously may permit this region of the proximal apex to rotate or bend to facilitate coupling to the coiled member 40, in the manner described above for the proximal extension segment 74 of FIGS. 6-8.

Referring now to FIG. 10, an alternative stent 160' is identical to the stent 160 of FIG. 9, with the exception that alternative proximal apices 161' comprise different axial lengths relative to one another. In the example of FIG. 10, each of the alternative proximal apices 161' comprises a progressively larger axial length, such that a first proximal apex 161a' comprises the smallest axial length, while the last proximal apex 161n' comprises the greatest axial length. Axial lengths of relatively thin strut segments 188' and their associated notched regions 189' may be varied to achieve the length differential between adjacent proximal apices 161a' through 161n', which yields a staggered axial positioning of the coupling members 162 of each apex, as shown in FIG. 10. The first proximal apex 161a' is loaded onto the coiled member 40 in the manner described above via engagement with the coupling member 162, and each subsequent proximal apex 161 is secured to the coiled member 40 until the final proximal apex 161n' is secured to the coiled member.

The axial length differential between coupling members 162 of adjacent proximal apices 161a' through 161n' can be determined according to the formula $i=p/n$, where "i" is the axial length between coupling members 162 of adjacent proximal apices 161a' through 161n', "p" is the pitch of the coiled member, and "n" is the number of proximal apices. For example, where there are twelve proximal apices 161a' through 161n', the value of "i" may equal 0.167 mm where the pitch of the coiled member is 2.0 mm, i.e., $i=p/n$ corresponds to 0.167 mm=2.0 mm/12.

Advantageously, by modifying the axial length between adjacent proximal apices 161a' through 161n', and yielding the staggered axial positioning of the coupling members 162 of each apex, capture of the coupling members 162 may be facilitated during securement to the coiled member 40. Further, the coupling members 162 can endure lower strains since the first proximal apex 161a' does not have to bend more to accommodate other points during the loading process. The proximal apices 161a' through 161n' can therefore be positioned in a uniform radial manner about the coiled member 40.

Referring now to FIGS. 11-13, an alternative stent 260 is similar to the stent 160' of FIG. 10, with like reference numerals designating corresponding parts, and with some notable exceptions described below. The stent 260 comprises a plurality of strut segments that enable expansion of the stent 260 from a delivery state to a deployed state. While several strut segments are shown in FIG. 11, and are generally similar to the strut segments 165 and 166 of the stent 160' of FIG. 10, select exemplary struts 266a-266e of FIG. 11 will be described further below.

The stent 260 further comprises at least one barb 267, and a select first barb 267a and its placement will be described further herein. The first barb 267a may be integrally formed with at least one of the strut segments, for example, by laser cutting, as generally shown herein. Alternatively, the first barb 267a may be externally formed and secured to a strut segment, for example, by a solder, weld, mechanical attachment, or the like. In the embodiment of FIG. 11, the first barb 267a has a base formed near a proximal apex 285 of the stent 260, and the first barb 267a extends in a distal direction such that a sharpened tip 275 is oriented distally.

In one embodiment, each of proximal apices 261a-261n comprises a coupling member 262, which may be similar to the coupling member 162 explained in FIG. 10 above. Each of distal apices 263 comprises a suture bore 264, an imaging marker 268, and an integral barb 269, as generally described in the embodiment of FIG. 10 above.

In the example of FIG. 11, the stent 260 comprises eight proximal apices 261a through 261n, which comprise different axial lengths relative to one another, as described above with respect to the embodiment of FIG. 10. In particular, each of the proximal apices 261a through 261n comprises a progressively larger axial length, thus yielding a staggered axial positioning of the coupling members 262 of each apex, as generally described in FIG. 10 above. The first proximal apex 261a is loaded onto the coiled member 40 in the manner described above via engagement with the coupling member 262, and each subsequent proximal apex 261 is secured to the coiled member 40 until the final proximal apex 261n is secured to the coiled member. The axial length differential between coupling members 262 may be determined according to the formula $i=p/n$, as explained with respect to FIG. 10 above.

In the example of FIGS. 11-13, five exemplary strut segments 266a-266e are highlighted to describe features of this embodiment. A pattern of the stent 260 is formed such that the first barb 267a is disposed at least partially laterally between the first and second strut segments 266a and 266b in a non-stacked state of FIG. 11. In the non-stacked state, the first and second strut segments 266a and 266b are neither partially nor fully overlapping relative to one another, as contrasted with a stacked delivery state shown in the embodiment of FIG. 12 in which the first and second strut segments 266a and 266b at least partially overlap relative to one another.

Figure 15:
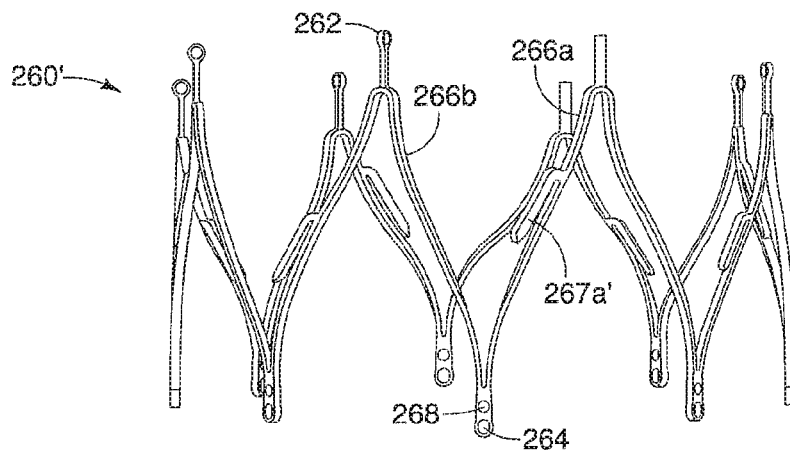
FIG. 15 is side view of the stent of FIG. 14 in a deployed state.

It should be noted that the stent 260 has a deployed state, similar to the deployed state shown in FIG. 15 for an alternative stent 260', in which the strut segments 266 flare out further with respect to one another. In the deployed state of the stent 260, as with the non-stacked state of FIG. 11, the first and second strut segments 266a and 266b are neither partially nor fully overlapping relative to one another. In the non-stacked states shown in FIGS. 11 and 15, the first barb 267a is disposed at least partially laterally between the first and second strut segments 266a and 266b.

Additionally, in the non-stacked state, a third strut segment 266c is disposed on a side of the second strut segment 266b opposing the first strut segment 266a, as shown in FIG. 11. Portions of the second and third strut segments 266b and 266c meet up with one another to form a proximal apex 285, which also includes a base portion of a second barb 267b, as shown in FIG. 11. Further, in the non-stacked state, a fourth strut segment 266d is disposed on a side of the third strut segment 266c opposing the second strut segment 266b, as shown in FIG. 11.

In accordance with one aspect, a frontal surface of the first strut segment 266a may be positioned at least partially behind a rear surface of another strut segment in the stacked delivery state. For example, the frontal surface of the first strut segment 266a may be positioned at least partially behind the second and third strut segments 266b and 266c in the stacked delivery state, as depicted in FIG. 12. Further, frontal surfaces of the second and third strut segments 266b and 266c may be positioned at least partially behind rear surfaces of the fourth and fifth strut segment 266d and 266e in the delivery state, as depicted in FIG. 12. In this manner, the stent 260 is circumferentially compressed in a type of "fan-blade arrangement" in the delivery state, as depicted from a top view of FIG. 13, in which certain apices are at least partially stacked behind one another. It is noted that the coupling members 262 are omitted in FIG. 13 for illustrative purposes.

In accordance with one aspect, the sharpened tip 275 of the first barb 267a may be aligned at least partially circumferentially behind at least one strut segment in the delivery state, such that the sharpened tip 275 is not radially exposed to a user. In the example of FIGS. 11-13, the sharpened tip 275 of the first barb 267a may be aligned circumferentially behind at least one of the second, third or fourth strut segments 266b-266d, as depicted in FIG. 12. In one technique, at least a portion of the first barb 267a is disposed between the second strut segment 266b and the third strut segment 266c in the delivery state, as can be seen in FIG. 12, in which case the first barb 267a is positioned behind the fourth strut segment 266d.

Notably, the first barb 267a may change positions relative to at least one strut segment between the non-stacked state and the stacked delivery state. As one example, the first barb 267a is disposed adjacent and parallel to the first strut segment 266a, and is positioned at least partially laterally between the first and second strut segments 266a and 266b, in the non-stacked states of FIG. 11 and FIG. 15. However, the first barb 267a has a different position in which it is at least partially disposed on an opposing side of the second strut segment 266b, i.e., between the second and third strut segments 266a and 266b, in the stacked delivery state, as depicted in FIG. 12. In this example, a majority of the first barb 267a is disposed on the opposing side of the second strut segment 266b and longitudinally adjacent to the second strut segment 266b in the delivery state. In effect, by compressing the stent 260 circumferentially in the "fan-blade arrangement" for the stacked delivery state, the first barb 267a may temporarily change positioning with respect to one or more strut segments 266, as compared to its position in the non-stacked state. Using this technique, the sharpened tip 275 of the first barb 267a may be hidden circumferentially behind one or more strut segments 266 during delivery.

In a similar manner, the other barbs 267 of the stent 260 may also be hidden circumferentially behind other strut segments during delivery. As another example, the second barb 267b, which is disposed adjacent to the third strut segment 266c in the non-stacked state, may be nested at least partially between the fourth and fifth strut segments 266d and 266e in the stacked delivery state shown in FIG. 12, and may be circumferentially covered by a sixth strut segment that would be disposed in front of the fourth and fifth strut segments 266d and 266e in FIG. 12.

Advantageously, using the technique of FIGS. 11-13, one or more barbs 267 may be hidden circumferentially behind one or more strut segments during delivery, in manners such that the sharpened tips 275 are not exposed during delivery, thereby providing a safer delivery. Additionally, the design of the stent 260 alone provides the ability to cover the barbs 267 during delivery without the need for a separate outer sheath or cap to hide the barbs prior to deployment.

Still further, by covering the barbs 267 during delivery in this manner, repositioning ability of the stent 260 may be enhanced prior to final deployment. In particular, any number of repositioning attempts may be made before final deployment of the stent 260 since the sharpened tips 275 of the barbs 267 are not exposed and do not prematurely engage a vessel wall.

Further, when the coiled member 40 described above is used to deploy the stent 260, it should be noted that a barb 267 of the stent will only be exposed when strut segments that are at least one or two positions before the strut segment carrying the barb are deployed. For example, in the embodiment of FIGS. 11-13, the first barb 267a will only be exposed to a vessel wall when one of the coupling members 262 most directly restraining the fourth strut segment 266d is released, since that fourth strut segment 266d may be circumferentially covering the first barb 267a as described in FIG. 12 above. When the next adjacent coupling member 262 is released, the second and third strut segments 266b and 266c will be released, thereby more fully exposing the first barb 267a. Finally, release of the coupling member 262 that is most directly restraining the first barb 267a allows the first barb 267a to engage tissue. Therefore, by using the coiled member 40 to deploy the stent 260, the barbs 267 can be progressively exposed after certain coupling members 262 are disengaged from the coiled member 40, thereby allowing barbs 267 to be exposed and engage tissue one at a time in a controlled manner.

In one embodiment, the final barb 267n may be either be blunt or rounded, as depicted in FIG. 11 and FIG. 13, or missing altogether. According to the stacking technique above, the final barb 267n may be adjacent to the final strut to be loaded and would not be covered by a subsequently loaded strut. Therefore, by having the final barb 267n be blunt, rounded or missing, there is no sharp tip exposed circumferentially that may cause damage during delivery.

Figure 14:
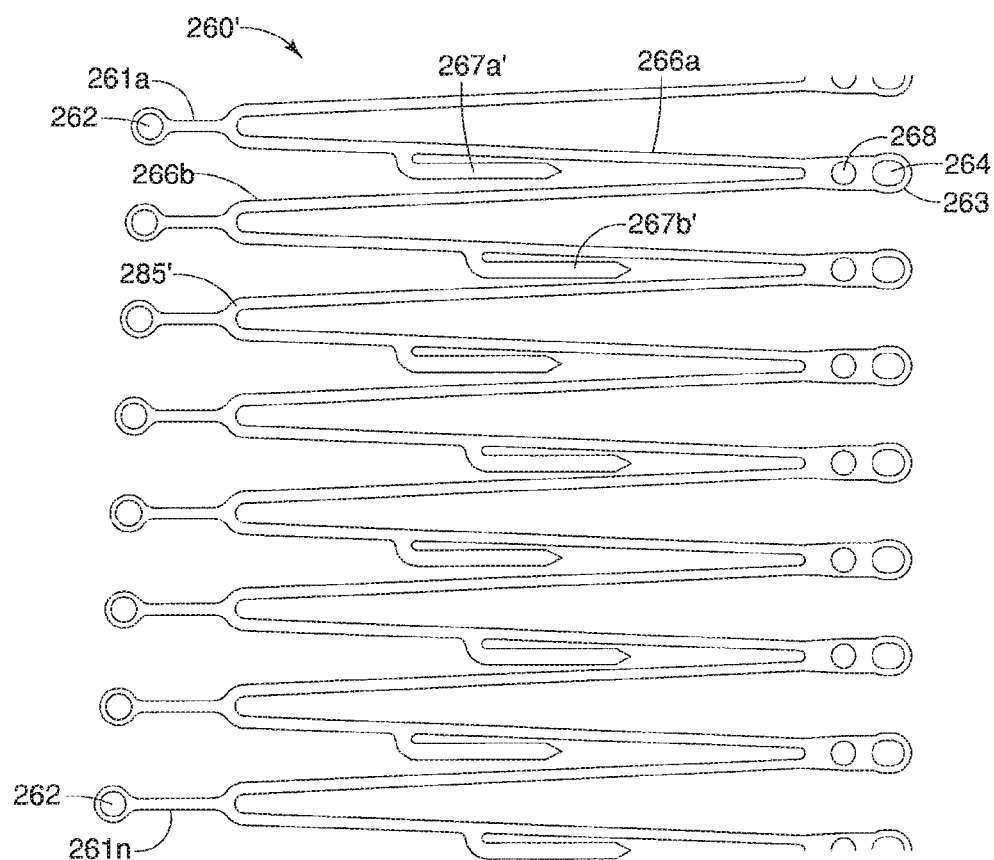
FIG. 14 is a side view of a further alternative stent, shown in a flattened and compressed state, which has barbs that are protected during delivery.

Referring now to FIGS. 14-15, an alternative embodiment of a stent 260' is shown and described. The stent 260' is substantially identical to the stent 260 of FIGS. 11-13, with a main exception that alternative barbs 267' are positioned further distally than the barbs 267 are positioned in the embodiment of FIGS. 11-13. Accordingly, alternative proximal apices 285' of FIGS. 14-15 may be thinner than the apices 285 of FIG. 11, since they do not need to accommodate the base of a barb. Further, the alternative stent 260' may comprise barbs 267a' and 267b' that are longitudinally offset from one another, as depicted in FIG. 14, which may facilitate nesting of adjacent barbs during loading. In use, the strut segments of the stent 260' may be stacked in a manner similar to the stacked delivery state of the strut segments 266 of the stent 260, and the barbs 267' of the stent 260' may be hidden relative to other strut segments in the manner described above with respect to the barbs 267 of FIGS. 11-13.

While various embodiments of the invention have been described, the invention is not to be restricted except in light of the attached claims and their equivalents. Moreover, the advantages described herein are not necessarily the only advantages of the invention and it is not necessarily expected that every embodiment of the invention will achieve all of the advantages described.

We claim:

1. A method for delivering a stent, comprising:
   providing a stent in a delivery state, wherein the stent comprises a plurality of interconnected strut segments that enable expansion of the stent from the delivery state to a deployed state;
   stacking a frontal surface of a first strut segment at least partially behind a rear surface of a second strut segment in the delivery state;
   aligning a sharpened tip of a first barb at least partially circumferentially behind at least one strut segment in the delivery state such that the sharpened tip is not radially exposed; and
   expanding the stent from the delivery state to a deployed state, wherein the first barb is exposed to a patient in the deployed state.

2. The method of claim 1, wherein the first barb is adjacent and parallel to the first strut segment in the deployed state.

3. The method of claim 1, wherein the first barb is disposed at least partially laterally between the first and second strut segments in the deployed state, and wherein the first barb is at least partially disposed on an opposing side of the second strut segment in the delivery state.

4. The method of claim 3, wherein a majority of the first barb is disposed on the opposing side of the second strut segment and longitudinally adjacent to the second strut segment in the delivery state.

5. The method of claim 3, comprising:
   a third strut segment, wherein portions of the second and third strut segments meet up with one another to form a proximal apex of the stent,
   wherein the third strut segment is on a side of the second strut segment opposing the first strut segment, and
   wherein at least a portion of the first barb is disposed between the second and third strut segments in the delivery state.

6. The method of claim 5, further comprising a fourth strut segment, wherein the fourth strut segment is on a side of the third strut segment opposing the second strut segment, and wherein at least a portion of the fourth strut segment circumferentially covers the first barb in the delivery state.

7. The method of claim 1, wherein the stent is configured to be releasably secured to a portion of a coiled member during delivery, wherein one of proximal or distal ends of the stent comprises a plurality of apices that each comprises a coupling member that is releasably secured to the coiled member.

8. The method of claim 7, where longitudinal positions of the coupling members of adjacent apices are axially staggered relative to each other.

9. The method of claim 8, wherein the axial staggering length differential between adjacent apices is calculated based on a formula factoring into account at least the pitch of the coiled member.

10. The method of claim 7, wherein the step of expanding the stent from the delivery state to a deployed state further comprises releasing the plurality of apices that each comprises a coupling member from the coiled member.

11. The method of claim 1, wherein a final strut segment to be loaded to a delivery system comprises one of a rounded or blunt or missing barb.

12. A method for delivering a stent, comprising:
    providing a stent in a delivery state, wherein the stent comprises a plurality of interconnected strut segments that enable expansion of the stent from a delivery state to a deployed state;
    positioning a first barb at least partially laterally between first and second strut segments in the deployed state; and
    positioning the first barb at least partially on an opposing side of the second strut segment in the delivery state.

13. The method of claim 12, wherein a sharpened tip of the first barb is aligned at least partially circumferentially behind at least one strut segment in the delivery state such that the sharpened tip is not radially exposed.

14. The method of claim 12, wherein a frontal surface of the first strut segment is at least partially stacked behind a rear surface of the second strut segment in the delivery state.

15. The method of claim 12, wherein a majority of the first barb is disposed on the opposing side of the second strut segment and longitudinally adjacent to the second strut segment in the delivery state.

16. The method of claim 12, comprising:
    a third strut segment, wherein portions of the second and third strut segments meet up with one another to form a proximal apex of the stent,
    wherein the third strut segment is on a side of the second strut segment opposing the first strut segment, and
    wherein at least a portion of the first barb is disposed between the second and third strut segments in the delivery state.

17. The method of claim 16, further comprising a fourth strut segment, wherein the fourth strut segment is on a side of the third strut segment opposing the second strut segment, and
    wherein at least a portion of the fourth strut segment circumferentially covers the first barb in the delivery state.

18. The method of claim 12, wherein the first barb is integrally formed with at least one of the strut segments.

19. The method of claim 12, wherein the first barb is adjacent and parallel to the first strut segment in the deployed state.

* * * * *